US012467914B2

(12) United States Patent
Ma et al.

(10) Patent No.: US 12,467,914 B2
(45) Date of Patent: Nov. 11, 2025

(54) SEGMENTED THERMAL PRESSURIZED HYDROCARBON GENERATION SIMULATION APPARATUS AND METHOD

(71) Applicant: GUANGZHOU INSTITUTE OF GEOCHEMISTRY, CHINESE ACADEMY OF SCIENCES, Guangdong (CN)

(72) Inventors: Weijiao Ma, Guangdong (CN); Jinzhong Liu, Guangdong (CN); Yunpeng Wang, Guangdong (CN); Qiang Wang, Guangdong (CN); Cui Weng, Guangdong (CN); Yong Li, Guangdong (CN)

(73) Assignee: GUANGZHOU INSTITUTE OF GEOCHEMISTRY, CHINESE ACADEMY OF SCIENCES, Guangzhou (CN)

( * ) Notice: Subject to any disclaimer, the term of this patent is extended or adjusted under 35 U.S.C. 154(b) by 0 days.

(21) Appl. No.: 19/000,436

(22) Filed: Dec. 23, 2024

(65) Prior Publication Data

US 2025/0321215 A1 Oct. 16, 2025

(30) Foreign Application Priority Data

Apr. 11, 2024 (CN) ........................ 202410434942.4

(51) Int. Cl.

| | |
|---|---|
| ***G01N 33/24*** | (2006.01) |
| ***G01N 3/18*** | (2006.01) |
| ***G01N 25/00*** | (2006.01) |

(52) U.S. Cl.
CPC ............... *G01N 33/24* (2013.01); *G01N 3/18* (2013.01); *G01N 25/00* (2013.01)

(58) Field of Classification Search
None
See application file for complete search history.

(56) References Cited

U.S. PATENT DOCUMENTS

2019/0187039 A1 6/2019 Su et al.

FOREIGN PATENT DOCUMENTS

| | | | |
|---|---|---|---|
| CN | 101149363 | A | 3/2008 |
| CN | 101402026 | A | 4/2009 |
| CN | 101520962 | A | 9/2009 |
| CN | 103454399 | A | 12/2013 |

(Continued)

*Primary Examiner* — Erica S Lin
(74) *Attorney, Agent, or Firm* — IPRTOP LLC

(57) ABSTRACT

A segmented thermal pressurized hydrocarbon generation simulation apparatus comprises a base, an insulation plate, three temperature and pressure control modules, two pressure boosted and blocking modules, a gold tube for sampling loading, and a control computer. A method applies different temperatures and pressures to the hydrocarbon generation zone, oil storage zone, and gas storage zone of the gold tube. The generated oil and gas flow from the hydrocarbon generation zone through the first blocking zone into the oil storage zone and be stored and altered under specific temperature and pressure conditions in the oil storage zone, and subsequently, the gas passes through the second blocking zone into the gas storage zone for storage. The first blocking zone and the second blocking zone are controlled by the pressure boosted and blocking modules, allowing the transfer of oil and gas from the hydrocarbon generation zone to the oil storage zone as needed.

6 Claims, 3 Drawing Sheets

(56) References Cited

FOREIGN PATENT DOCUMENTS

| | | | |
|---|---|---|---|
| CN | 110595938 | A | 12/2019 |
| CN | 115128243 | A | 9/2022 |
| WO | 2022262146 | A1 | 12/2022 |

SEGMENTED THERMAL PRESSURIZED HYDROCARBON GENERATION SIMULATION APPARATUS AND METHOD

TECHNICAL FIELD

The present invention relates to the technical field of hydrocarbon generation thermal simulation experiments for hydrocarbon source rock, and particularly to a segmented thermal pressurized hydrocarbon generation simulation apparatus and method.

BACKGROUND

A hydrocarbon generation thermal simulation experiment for hydrocarbon source rock is an important method in oil and gas geology and geochemistry researches. At present, in main thermal simulation experimental methods at home and abroad, a sample cylinder is mainly used to pressurize and heat the hydrocarbon source rock, and generated oil and gas may stay in the sample cylinder or be expelled out of the reaction system according to certain rules.

The main problem of the above experimental methods is that there is no independent reservoir, and there are only two options for the generated oil and gas, which means that the generated oil and gas exist in a hydrocarbon source rock zone to be continuously heated, or the generated oil and gas are expelled out of a heating zone and enter a normal temperature or freezing zone. In an actual stratum, a hydrocarbon generation zone and a reservoir zone both have certain temperature and pressure, but the temperature and pressure of the reservoir are lower than those of the hydrocarbon generation zone. Under the drive by this pressure difference, the generated oil and gas are transferred from the hydrocarbon generation zone to the reservoir, and the temperature and pressure differences between the hydrocarbon generation zone and the reservoir have important impacts on both hydrocarbon expulsion efficiency and selective hydrocarbon expulsion. In addition, currently popular piston-type thermal pressurized hydrocarbon generation experimental apparatuses still have the problems of complex structure, difficulty to avoid oil and gas leakage, difficult operation, and the like.

SUMMARY

The present invention aims to provide a segmented thermal pressurized hydrocarbon generation simulation apparatus and method, which are simple to operate and can truly simulate a geochemical process of hydrocarbon generation-oil expulsion-gas expulsion in a stratum and the evolution of oil and gas in a reservoir.

In order to achieve the above technical object, the following technical solution is used in the present invention: a segmented thermal pressurized hydrocarbon generation simulation apparatus comprises a base, an insulation chamber fixed on the base with front and rear doors, three temperature and pressure control modules, two pressure boosted and blocking modules, a gold tube for holding sample, and a main control computer. Three temperature and pressure control modules are spaced apart and installed within the insulation chamber. A pressure boosted and blocking module is located between each adjacent pair of temperature and pressure control modules. Each temperature and pressure control module comprises a lower mold base and an upper mold base, with electric heating rods and thermocouples installed on both the lower and upper mold bases. Both the lower mold base and the upper mold base are provided with arc-shaped positioning grooves for positioning the gold tube. The pressure boosted and blocking module comprises a lower support base and an upper pressure head. Five piston-type hydraulic servo pumps are arranged above the insulation chamber, each equipped with a pressure sensor. The piston rods of the piston-type hydraulic servo pumps extend into the insulation chamber. The upper mold bases of the three temperature and pressure control modules and the upper pressure heads of the two pressure boosted and blocking modules are respectively connected to the piston rods of the five piston-type hydraulic servo pumps. The gold tube is divided into a hydrocarbon generation zone, a first blocking zone, an oil storage zone, a second blocking zone, and a gas storage zone. During the experiment, the hydrocarbon generation zone, oil storage zone, and gas storage zone are respectively positioned within the three temperature and pressure control modules. The first blocking zone and the second blocking zone are respectively positioned on the lower support bases of the two blocking modules. The thermocouples are capable of collecting temperature signals and transmitting them to the main control computer. The activation and deactivation of the electric heating rods and the piston-type hydraulic servo pumps are controlled by the main control computer.

Further, the gold tube has an outer diameter of 8 mm, a wall thickness of 0.8 mm and a length of 150 mm.

The present invention further discloses a segmented thermal pressurized hydrocarbon generation simulation method, comprising: using the segmented thermal pressurized hydrocarbon generation simulation apparatus, wherein the three temperature and pressure control modules are respectively labeled as a hydrocarbon generation module, an oil storage module and a gas storage module, and the two pressure boosted and blocking modules are labeled as a first pressure boosted and blocking module and a second pressure boosted and blocking module; wherein the hydrocarbon generation zone, first blocking zone, oil storage zone, second blocking zone, and gas storage zone of the gold tube are respectively associated with piston-type hydraulic servo pumps labeled as a first piston-type hydraulic servo pump, a second piston-type hydraulic servo pump, a third piston-type hydraulic servo pump, a fourth piston-type hydraulic servo pump, and a fifth piston-type hydraulic servo pump respectively; and the experimental method includes the following steps:

(1) Welding the left end of the gold tube; loading hydrocarbon source rock, oil reservoir rock and gas reservoir rock respectively into the hydrocarbon generation zone, oil storage zone, and gas storage zone of the gold tube; placing quartz wool on both sides of the first blocking zone and the second blocking zone; subsequently vacuumizing the gold tube; and finally sealing the right end of the gold tube by welding;

(2) Wrapping graphite foil around the exterior of the gold tube, and then placing the gold tube wrapped with graphite foil into the arc-shaped positioning groove of the experimental apparatus;

(3) Setting the temperature and pressure values for the hydrocarbon generation module, oil storage module and gas storage module, and also setting the pressure values for the first pressure boosted and blocking module and the second pressure boosted and blocking module; and controlling the five piston-type hydraulic servo pumps to apply pressure and starting the corresponding electric heating rods for heating, all by means of the main control computer;

(4) Starting the hydrocarbon generation thermal simulation; as the temperature increases, the hydrocarbon generation zone of the gold tube expands due to pressure increase from hydrocarbon generation, causing the pressure of the corresponding first piston-type hydraulic servo pump to gradually increase; when the first piston-type hydraulic servo pump reaches a preset pressure, the piston rod of the second piston-type hydraulic servo pump rises, releasing oil and gas into the oil storage zone of the gold tube; when the pressure of the third piston-type hydraulic servo pump reaches a preset pressure, the piston rod of the fourth piston-type hydraulic servo pump rises, releasing gas into the gas storage zone of the gold tube;

(5) Maintaining step (4) until the hydrocarbon generation experiment is completed;

(6) Lowering the temperature of the hydrocarbon generation module (M1) segment to stopping the hydrocarbon generation process; the piston rod of the fourth piston-type hydraulic servo pump descends and the piston rod of the second piston-type hydraulic servo pump rises, thereby initiating the pure hydrocarbon expulsion process;

(7) After the hydrocarbon generation thermal simulation process is completed, opening the door of the insulation chamber and spraying liquid nitrogen onto the three temperature and pressure control modules; when the temperature of the hydrocarbon generation module, oil storage module and gas storage module is lower than or equal to −5° C., raising the piston rods of all piston-type hydraulic servo pumps to the highest position; removing the gold tube and immediately clamping the positions of the first and second blocking zones with flat-nose clamps; and (8) Placing the gold tube along with the clamps into a portable refrigerator and transferring it into another device for respective analysis of oil and gas in the gas storage zone, oil storage zone and hydrocarbon generation zone of the gold tube.

Further, a molecular sieve is placed at the left end of the gas storage zone of the gold tube to prevent large molecular oil from entering the gas storage zone.

The present invention has the beneficial effects that: the solution of the present invention is simple to operate, and except the processes of filling the gold tube and removing the gold tube, other operations are all automatically carried out under the control of the main control computer, thereby reducing labor consumption and improving a success rate of the experiment.

The method of the present invention applies different temperatures and pressures to the hydrocarbon generation zone, oil storage zone and gas storage zone of the gold tube, controlled by the computer. The generated oil and gas from the hydrocarbon source rock under temperature and pressure conditions flow from the hydrocarbon generation zone through the first blocking zone into the oil storage zone. The oil continues to be stored and altered under specific temperature and pressure conditions in the oil storage zone, and subsequently, the gas passes through the second blocking zone into the gas storage zone for storage. The communication or closure of the first blocking zone and the second blocking zone is controlled by the pressure boosted and blocking modules, allowing the transfer of oil and gas from the hydrocarbon generation zone to the oil storage zone as needed. The whole experimental process may truly simulate a geochemical process of hydrocarbon generation, hydrocarbon expulsion, storage and transformation, and gas expulsion and storage in a stratum. Finally, data of gas, expelled hydrocarbon and retained hydrocarbon of an experimental sample may be obtained. In addition, all experiments are carried out in a closed system, which avoids the leakage loss of oil and gas during the experiment.

BRIEF DESCRIPTION OF THE DRAWINGS

The present invention is further described in detail hereinafter with reference to the drawings.

DETAILED DESCRIPTION

The present invention is further described in detail hereinafter with reference to the drawings.

As shown in FIG. 1 to FIG. 4, a segmented thermal pressurized hydrocarbon generation simulation apparatus of the present invention comprises a base 1, an insulation chamber 2 fixed on the base with front and rear doors, three temperature and pressure control modules, two pressure boosted and blocking modules, a gold tube 5 for holding sample and a main control computer.

Figure 5:
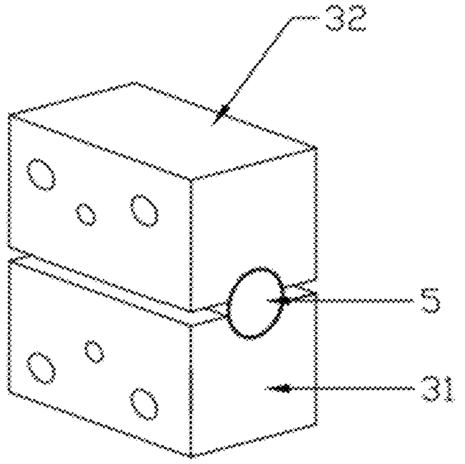
FIG. 5 is a schematic diagram of a state in which the upper mold base and the lower mold base of the temperature and pressure control module just make contact with a gold tube in the present invention.

Each temperature and pressure control module comprises a lower mold base 31 and an upper mold base 32, the lower mold base 31 and the upper mold base 32, with electric heating rods and thermocouples installed on both the lower mold base 31 and the upper mold base 32. Both the lower mold base 31 and the upper mold base 32 are provided with arc-shaped positioning grooves 33 for positioning the gold tube. When the gold tube 5 is arranged in two arc-shaped positioning grooves 33, the state is as shown in FIG. 5. The pressure boosted and blocking module comprises a lower support base 41 and an upper pressure head 42.

The three temperature and pressure control modules are labeled as a hydrocarbon generation module M1, an oil storage module M2 and a gas storage module M3 respectively, and spaced apart and installed within the insulation chamber, and the two pressure boosted and blocking modules are labeled as a first blocking module Z1 and a second blocking module Z2. The first blocking module Z1 is arranged between the hydrocarbon generation module M1 and the oil storage module M2; and the second blocking module Z2 is arranged between the oil storage module M2 and the gas storage module M3.

Five piston-type hydraulic servo pumps are fixed on the base 1 through supports (not shown in the drawings), and the five piston-type hydraulic servo pumps are arranged above the insulation chamber 2. The five piston-type hydraulic servo pumps are respectively labeled as a first piston-type hydraulic servo pump P1, a second piston-type hydraulic servo pump P2, a third piston-type hydraulic servo pump P3, a fourth piston-type hydraulic servo pump P4 and a fifth piston-type hydraulic servo pump P5. The first piston-type hydraulic servo pump P1, the second piston-type hydraulic servo pump P2, the third piston-type hydraulic servo pump P3, the fourth piston-type hydraulic servo pump P4 and the fifth piston-type hydraulic servo pump P5 are respectively provided with a first pressure sensor S1, a second pressure sensor S2, a third pressure sensor S3, a fourth pressure sensor S4 and a first pressure sensor S5.

A top surface of the insulation chamber 2 is provided with five through holes, and the five piston-type hydraulic servo pumps extend into the insulation chamber 2 from the five through holes. The upper mold base of the hydrocarbon generation module M1, the upper pressure head of the first blocking module Z1, the upper mold base of the oil storage module M2, the upper pressure head of the first blocking module Z2 and the upper mold base of the gas storage module M3 are respectively connected to corresponding piston rods of the first piston-type hydraulic servo pump P1, the second piston-type hydraulic servo pump P2, the third piston-type hydraulic servo pump P3, the fourth piston-type hydraulic servo pump P4 and the fifth piston-type hydraulic servo pump P5.

The gold tube 5 is divided into a hydrocarbon generation zone, a first blocking zone, an oil storage zone, a second blocking zone, and a gas storage zone. During the experiment, the hydrocarbon generation zone, oil storage zone and gas storage zone are respectively positioned within the hydrocarbon generation module M1, oil storage module M2 and gas storage module M3. The first blocking zone and the second blocking zone are respectively positioned on the lower support bases of the first blocking module Z1 and the second blocking module Z2.

The thermocouples are capable of collecting temperature signals and transmitting them to the main control computer. The activation and deactivation of the electric heating rods and the piston-type hydraulic servo pumps are controlled by the main control computer.

Figure 1:
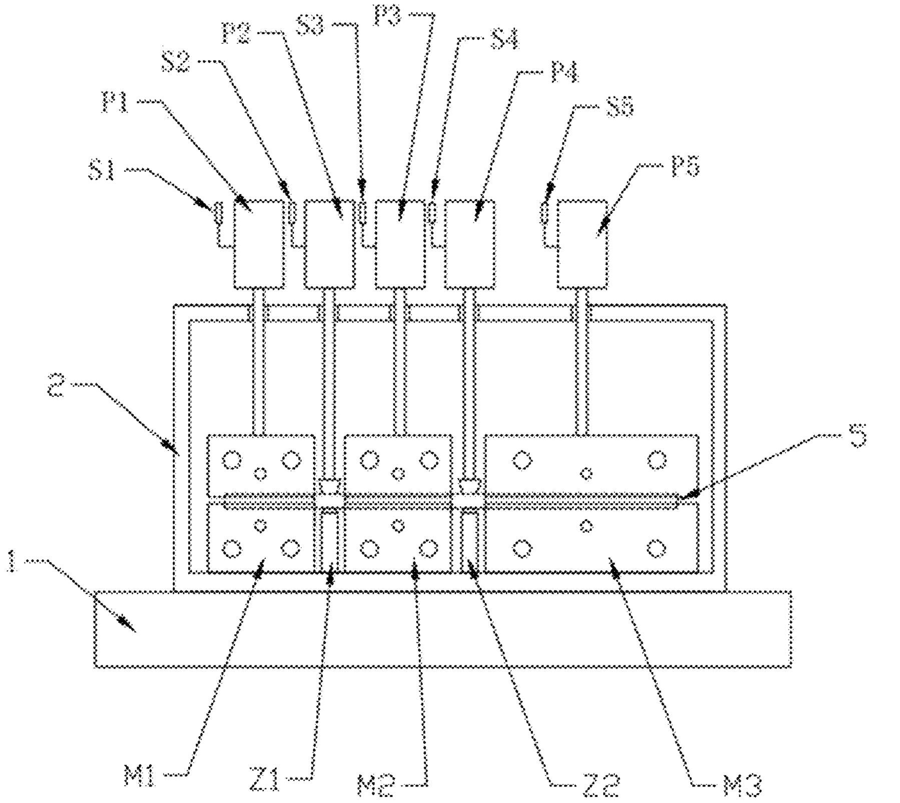
FIG. 1 is a schematic structural diagram of the present invention.
Figure 2:
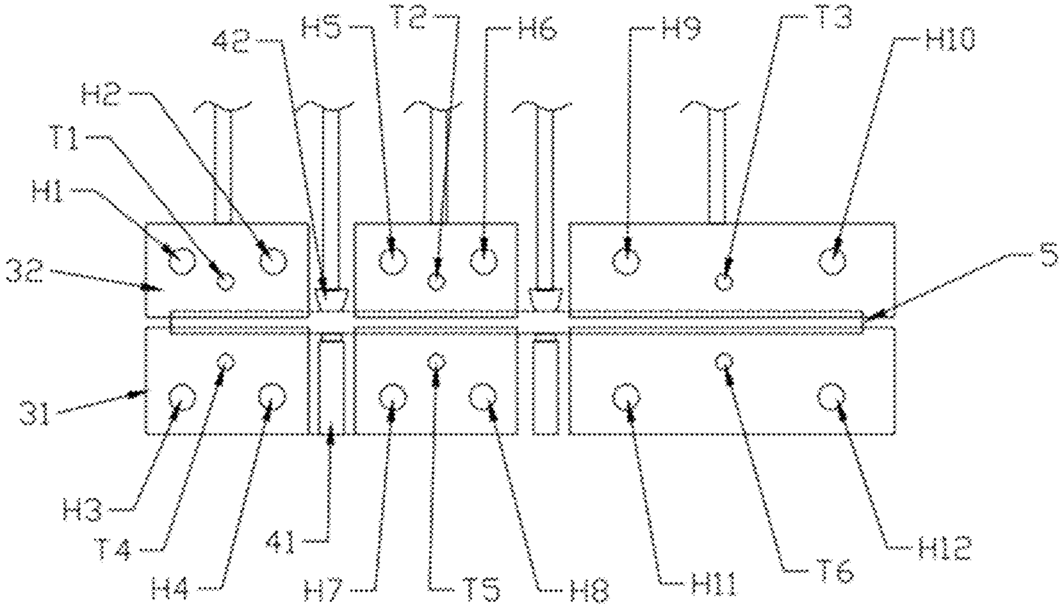
FIG. 2 is an enlarged view of three temperature and pressure control modules and two pressure boosted and blocking modules in FIG. 1.
Figure 3:
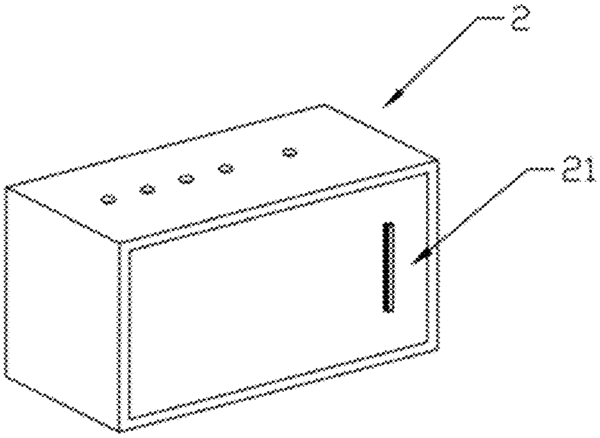
FIG. 3 is a schematic structural diagram of an insulation chamber in the present invention.
Figure 4:
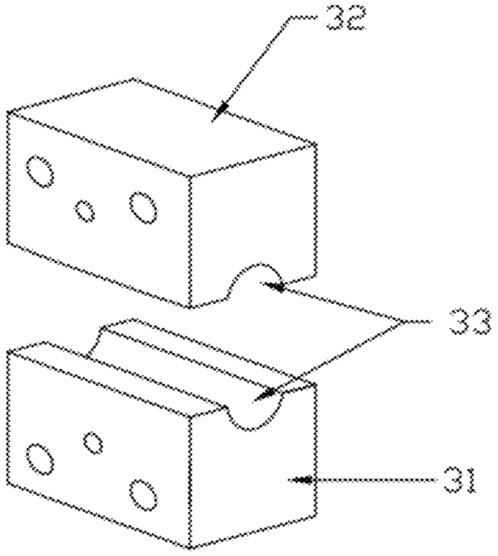
FIG. 4 is a schematic structural diagram of a lower mold base and an upper mold base of the temperature and pressure control module in the present invention.

Specifically, the lower mold base and the upper mold base of each temperature and pressure control module are both provided with two electric heating rods and one thermocouple. As shown in FIG. 1, the upper mold base of the hydrocarbon generation module M1 is provided with two electric heating rods H1 and H2 and a thermocouple T1; and the lower mold base of the hydrocarbon generation module M1 is provided with two electric heating rods H3 and H4 and a thermocouple T4. The upper mold base of the oil storage module M2 is provided with two electric heating rods H5 and H6 and a thermocouple T2; and the lower mold base of the oil storage module M2 is provided with two electric heating rods H7 and H8 and a thermocouple T5. The upper mold base of the gas storage module M3 is provided with two electric heating rods H9 and H10 and a thermocouple T3; and the lower mold base of the hydrocarbon generation module M1 is provided with two electric heating rods H11 and H12 and a thermocouple T6. The electric heating rods H1 to H12 may heat corresponding modules under the control of the main control computer, and the thermocouples T1 to T6 are used to monitor temperatures and feed the temperatures back to the main control computer; and the temperatures of the hydrocarbon generation module M1, oil storage module M2 and gas storage module M3 may be controlled independently.

The main control computer is capable of controlling the piston rods of the five piston-type hydraulic servo pumps to rise or descend respectively, and when the piston rods of the first piston-type hydraulic servo pump P1, the third piston-type hydraulic servo pump P3 and the fifth piston-type hydraulic servo pump P5 descend, the piston rods are capable of respectively driving the upper mold bases of the hydrocarbon generation module M1, oil storage module M2 and gas storage module M3 to move downwards, thereby applying pressures to the gold tube. When the piston rod of the second piston-type hydraulic servo pump P2 descends, the upper pressure head of the first blocking module Z1 is capable of being driven to move downwards, and in cooperation with the lower support base of the first blocking module Z1, the first blocking zone of the gold tube is capable of being compacted, which is equivalent to closing a passage between the hydrocarbon generation zone and the oil storage zone. When the piston rod of the second piston-type hydraulic servo pump P4 descends, the upper pressure head of the second blocking module Z2 is capable of being driven to move downwards, and in cooperation with the lower support base of the second blocking module Z2, the second blocking zone of the gold tube is capable of being compacted, which is equivalent to closing a passage between the oil storage zone and the gas storage zone.

Specifically, the gold tube has an outer diameter of 8 mm, a wall thickness of 0.8 mm and a length of 150 mm. A left side (hydrocarbon generation zone) of the gold tube is a space filled with a hydrocarbon source rock sample, and the sample is rock powder, small particles or small columns. A middle part (oil storage zone) of the gold tube is an oil reservoir space, which May be filled with sandstone, carbonate rock, and the like according to an actual situation of stratum. A right side (gas storage zone) of the gold tube is a gas reservoir space, which may be filled with sandstone, quartz sand, and the like as needed. The first blocking zone is arranged between the hydrocarbon generation zone and the oil storage zone, and the second blocking zone is arranged between the oil storage zone and the gas storage zone; and middle parts of the first blocking zone and the second blocking zone are cavities, and two ends of the first blocking zone and the second blocking zone are filled with quartz wool. During the experiment, the first blocking module Z1 and the second blocking module Z2 are capable of partially compacting the cavities to close the passages. In addition, during the experiment, graphite foil is wrapped around the exterior of the gold tube 5, and the graphite foil plays a role of buffering to protect the gold tube and transmit pressure and temperature.

The present invention further discloses a segmented thermal pressurized hydrocarbon generation simulation method, wherein the segmented thermal pressurized hydrocarbon generation simulation apparatus above is used in the experiment, and the experimental method comprises the following steps.

Figure 6:
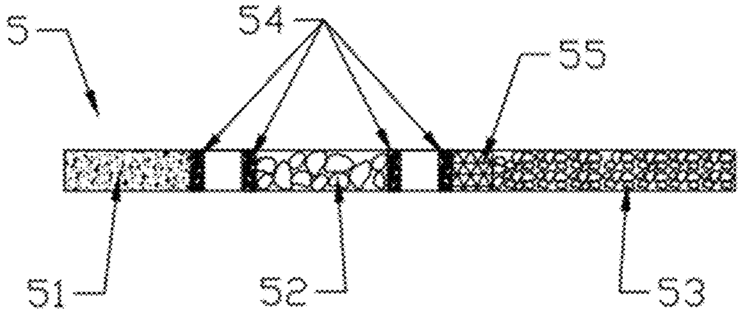
FIG. 6 is a schematic diagram of the gold tube filled with a sample and other materials in the present invention.

(1) A left end of the gold tube 5 is welded, hydrocarbon source rock 51, oil reservoir rock 52, and gas reservoir rock 53 are respectively loaded into the hydrocarbon generation zone, oil storage zone and gas storage zone of the gold tube, and quartz wool 54 is placed on both sides of the first blocking zone and the second blocking zone; and subsequently, the gold tube is vacuumized; and finally the right end of the gold tube is sealed by welding. In order to prevent large molecular oil from entering the gas storage zone during gas collection, a molecular sieve 55 may also be placed at the left end of the gas storage zone of the gold tube; and the state after material filling is as shown in FIG. 6.

(2) Graphite foil is wrapped around the exterior of the gold tube, and then the gold tube wrapped with the graphite foil is placed into the positioning groove of the experimental apparatus.

(3) The temperature and pressure values are set for the hydrocarbon generation module M1, oil storage module M2 and gas storage module M3, and the pressure values are also set for the first pressure boosted and blocking module Z1 and the second pressure boosted and blocking module Z2 are simultaneously set; and the five piston-type hydraulic servo pumps are controlled to apply pressure and the corresponding electric heating rods are started for heating, all by means of the main control computer. The pressures of the first piston-type hydraulic servo pump P1, the third piston-type hydraulic servo pump P3 and the fifth piston-type hydraulic servo pump P5 should be set according to a pressure of stratum in combination with an area ratio of a bottom receiving area of the gold tube to a telescopic rod of the servo pump. The pressures of the second piston-type hydraulic servo pump P2 and the fourth piston-type hydraulic servo pump P4 are set to be fixed, and the pressures of the second piston-type hydraulic servo pump P2 and the fourth piston-type hydraulic servo pump P4 are set to be 5 MP.

(4) The hydrocarbon generation thermal simulation is started; as the temperature increases, the hydrocarbon generation zone of the gold tube expands due to pressure increase from hydrocarbon generation, causing the pressure of the corresponding first piston-type hydraulic servo pump P1 to gradually increase; when the first piston-type hydraulic servo pump P1 reaches a preset pressure, the piston rod of the second piston-type hydraulic servo pump P2 rises, releasing oil and gas into the oil storage zone of the gold tube; when the pressure of the third piston-type hydraulic servo pump P3 reaches a preset pressure, the piston rod of the fourth piston-type hydraulic servo pump P4 rises, releasing gas into the gas storage zone of the gold tube.

(5) The step (4) is maintained until the hydrocarbon generation experiment is completed.

(6) After the hydrocarbon generation experiment is completed, the temperature of the hydrocarbon generation module M1 segment is lowered according to requirements of the experimental sample, and when the temperature is lowered to the preset value, the hydrocarbon generation process is stopped, the piston rod of the fourth piston-type hydraulic servo pump P4 descends and the piston rod of the second piston-type hydraulic servo pump P2 rises, thereby initiating the pure hydrocarbon expulsion process. A duration of the hydrocarbon expulsion process depends on actual experimental needs, which is generally 1 hour to 72 hours.

(7) After the hydrocarbon expulsion process is completed, the door 21 of the insulation chamber is opened, a liquid nitrogen cooling system is used to spray liquid nitrogen onto the three temperature and pressure control modules; when the temperature of the hydrocarbon generation module M1, oil storage module M2 and gas storage module M3 is lower than or equal to −5° C., the piston rods of all piston-type hydraulic servo pumps are raised to the highest position; the gold tube is removed and the positions of the first and second blocking zones with flat-nose clamps are immediately clamped.

(8) The gold tube is placed along with the clamps into a portable refrigerator and transferred to another device for respective analysis of oil and gas in the gas storage zone, the oil storage zone and hydrocarbon generation zone of the gold tube.

Specifically, the liquid nitrogen cooling system in the step (7) comprises a liquid nitrogen tank, a gas pipeline, a liquid nitrogen nozzle, a control valve, and the like. After the door 21 of the insulation chamber is opened, the liquid nitrogen nozzle is moved to a position in front of the door of the insulation chamber and oriented to the three temperature and pressure control modules, the control valve is opened, the liquid nitrogen is sprayed to cool the modules, and the control valve is closed when the three modules reach preset cooling temperatures.

The above contents are only used to illustrate the technical solutions of the present invention, and simple modifications or equivalent substitutions made by those of ordinary skills in the art do not depart from the essence and scope of the technical solutions of the present invention.

What is claimed is:

1. A segmented thermal pressurized hydrocarbon generation simulation apparatus comprising:

a base, an insulation chamber fixed on the base with a front and a rear doors, three temperature and pressure control modules, two pressure boosted and blocking modules, a gold tube for holding sample, and a main control computer;

the three temperature and pressure control modules are spaced apart and installed within the insulation chamber, with a first pressure boosted and blocking module of the two pressure boosted and blocking modules interposed between a first temperature and pressure control module and a second temperature and pressure control module of the three temperature and pressure control modules and a second pressure boosted and blocking module of the two pressure boosted and blocking modules interposed between the second temperature and pressure control module and a third temperature and pressure control module of the three temperature and pressure control modules, wherein each of the temperature and pressure control modules comprises a lower mold base and an upper mold base, with electric heating rods and thermocouples installed on both the lower and upper mold bases, both the lower mold base and the upper mold base are provided with arc-shaped positioning grooves for positioning the gold tube, each of the pressure boosted and blocking modules comprises a lower support base and an upper pressure head;

the insulation chamber is provided with five piston-type hydraulic servo pumps, wherein each of the piston-type hydraulic servo pumps is equipped with a pressure sensor and a piston rod of each of the piston-type hydraulic servo pumps extends into the insulation chamber, the upper mold bases of the three temperature and pressure control modules and the upper pressure heads of the two pressure boosted and blocking modules are respectively connected to the piston rods of the five piston-type hydraulic servo pumps;

the gold tube is divided into a hydrocarbon generation zone, a first blocking zone, an oil storage zone, a second blocking zone, and a gas storage zone, during an experiment, the hydrocarbon generation zone, oil storage zone, and gas storage zone are respectively positioned within the three temperature and pressure control modules, the first blocking zone and the second blocking zone are respectively positioned on the lower support bases of the two blocking modules, the thermocouples are capable of collecting temperature signals and transmitting them to the main control computer, activations and deactivations of the electric heating rods and the piston-type hydraulic servo pumps are controlled by the main control computer.

2. The segmented thermal pressurized hydrocarbon generation simulation apparatus according to claim 1, wherein the gold tube has an outer diameter of 8 mm, a wall thickness of 0.8 mm, and a length of 150 mm.

3. A segmented thermal pressurized hydrocarbon generation simulation method comprising:

using the segmented thermal pressurized hydrocarbon generation simulation apparatus according to claim 1, wherein the three temperature and pressure control modules are respectively labeled as a hydrocarbon generation module (M1), an oil storage module (M2), and a gas storage module (M3), and the two pressure boosted and blocking modules are labeled as a first pressure boosted and blocking module (Z1) and a second pressure boosted and blocking module (Z2);

wherein the hydrocarbon generation zone, first blocking zone, oil storage zone, second blocking zone, and gas storage zone of the gold tube are respectively associated with the piston-type hydraulic servo pumps labeled as a first piston-type hydraulic servo pump (P1), a second piston-type hydraulic servo pump (P2), a third piston-type hydraulic servo pump (P3), a fourth piston-type hydraulic servo pump (P4), and a fifth piston-type hydraulic servo pump (P5); an experimental method includes the following steps:

(1) welding a first end of the gold tube; loading a hydrocarbon source rock, an oil reservoir rock, and a gas reservoir rock respectively into the hydrocarbon generation zone, oil storage zone, and gas storage zone of the gold tube; placing a quartz wool on both sides of the first blocking zone and the second blocking zone; subsequently vacuuming the gold tube; and finally sealing a second end of the gold tube by welding;

(2) wrapping a graphite foil around an exterior of the gold tube, and then placing the gold tube wrapped with the graphite foil into the arc-shaped positioning groove of the apparatus for the method;

(3) setting a temperature and a pressure values for the hydrocarbon generation module (M1), the oil storage module (M2), and the gas storage module (M3), and also setting the pressure values for the first pressure boosted and blocking module (Z1) and the second pressure boosted and blocking module (Z2); controlling the five piston-type hydraulic servo pumps to apply pressure and starting the corresponding electric heating rods for heating, all by means of the main control computer;

(4) starting a hydrocarbon generation thermal simulation; as the temperature increases, the hydrocarbon generation zone of the gold tube expands due to pressure increase from hydrocarbon generation, causing a pressure of the corresponding first piston-type hydraulic servo pump (P1) to gradually increase; when the first piston-type hydraulic servo pump (P1) reaches a preset pressure, the piston rod of the second piston-type hydraulic servo pump (P2) rises, releasing oil and gas into the oil storage zone of the gold tube; when the pressure of the third piston-type hydraulic servo pump (P3) reaches a preset pressure, the piston rod of the fourth piston-type hydraulic servo pump (P4) rises, releasing gas into the gas storage zone of the gold tube;

(5) maintaining the step (4) until the hydrocarbon generation experiment is completed-;

(6) lowering the temperature of the hydrocarbon generation module (M1) segment to stop the hydrocarbon generation process; the piston rod of the fourth piston-type hydraulic servo pump (P4) descends and the piston rod of the second piston-type hydraulic servo (P2) rises, thereby initiating a pure hydrocarbon expulsion process;

(7) after the hydrocarbon expulsion process is completed, opening the door of the insulation chamber and spraying liquid nitrogen onto the three temperature and pressure control modules; when temperatures of the hydrocarbon generation module (M1), oil storage module (M2), and gas storage module (M3) are lower than −5° C., raising the piston rods of all piston-type hydraulic servo pumps to the highest position; removing the gold tube and immediately clamping positions of the first and second blocking zones with flat-nose clamps;

(8) placing the gold tube along with the flat-nose clamps into a portable refrigerator and transferring it to another device for respective analysis of oil and gas in the gas storage zone, oil storage zone, and hydrocarbon generation zone of the gold tube.

4. The segmented thermal pressurized hydrocarbon generation simulation apparatus according to claim 3, wherein a molecular sieve is placed at an end of the gas storage zone near the second blocking zone of the gold tube to prevent large molecular oil from entering the gas storage zone.

5. A segmented thermal pressurized hydrocarbon generation simulation method comprising:

using the segmented thermal pressurized hydrocarbon generation simulation apparatus according to claim 2, wherein the three temperature and pressure control modules are respectively labeled as a hydrocarbon generation module (M1), an oil storage module (M2), and a gas storage module (M3), and the two pressure boosted and blocking modules are labeled as a first pressure boosted and blocking module (Z1) and a second pressure boosted and blocking module (Z2);

wherein the hydrocarbon generation zone, first blocking zone, oil storage zone, second blocking zone, and gas storage zone of the gold tube are respectively associated with the piston-type hydraulic servo pumps labeled as a first piston-type hydraulic servo pump (P1), a second piston-type hydraulic servo pump (P2), a third piston-type hydraulic servo pump (P3), a fourth piston-type hydraulic servo pump (P4), and a fifth piston-type hydraulic servo pump (P5); an experimental method includes the following steps:

(1) welding a first end of the gold tube; loading a hydrocarbon source rock, an oil reservoir rock, and a gas reservoir rock respectively into the hydrocarbon generation zone, oil storage zone, and gas storage zone of the gold tube; placing a quartz wool on both sides of the first blocking zone and the second blocking zone; subsequently vacuuming the gold tube; and finally sealing a second end of the gold tube by welding;

(2) wrapping a graphite foil around an exterior of the gold tube, and then placing the gold tube wrapped with the graphite foil into the arc-shaped positioning groove of the apparatus for the method;

(3) setting a temperature and a pressure values for the hydrocarbon generation module (M1), the oil storage module (M2), and the gas storage module (M3), and also setting the pressure values for the first pressure boosted and blocking module (Z1) and the second pressure boosted and blocking module (Z2); controlling the five piston-type hydraulic servo pumps to apply pressure and starting the corresponding electric heating rods for heating, all by means of the main control computer;

(4) starting a hydrocarbon generation thermal simulation; as the temperature increases, the hydrocarbon generation zone of the gold tube expands due to pressure increase from hydrocarbon generation, causing a pressure of the corresponding first piston-type hydraulic servo pump (P1) to gradually increase; when the first piston-type hydraulic servo pump (P1) reaches a preset pressure, the piston rod of the second piston-type hydraulic servo pump (P2) rises, releasing oil and gas into the oil storage zone of the gold tube; when the pressure of the third piston-type hydraulic servo pump (P3) reaches a preset pressure, the piston rod of the fourth piston-type hydraulic servo pump (P4) rises, releasing gas into the gas storage zone of the gold tube;

(5) maintaining the step (4) until the hydrocarbon generation experiment is completed-;

(6) lowering the temperature of the hydrocarbon generation module (M1) segment to stop the hydrocarbon generation process; the piston rod of the fourth piston-type hydraulic servo pump (P4) descends and the piston rod of the second piston-type hydraulic servo pump (P2) rises, thereby initiating a pure hydrocarbon expulsion process;

(7) after the hydrocarbon expulsion process is completed, opening the door of the insulation chamber and spraying liquid nitrogen onto the three temperature and pressure control modules; when temperatures of the hydrocarbon generation module (M1), oil storage module (M2), and gas storage module (M3) are lower than −5° C., raising the piston rods of all piston-type hydraulic servo pumps to the highest position; removing the gold tube and immediately clamping positions of the first and second blocking zones with flat-nose clamps;

(8) placing the gold tube along with the flat-nose clamps into a portable refrigerator and transferring it to another device for respective analysis of oil and gas in the gas storage zone, oil storage zone, and hydrocarbon generation zone of the gold tube.

6. The segmented thermal pressurized hydrocarbon generation simulation apparatus according to claim 5, wherein a molecular sieve is placed at an end of the gas storage zone near the second blocking zone of the gold tube to prevent large molecular oil from entering the gas storage zone.

* * * * *